United States Patent [19]

Nevin

[11] Patent Number: 4,698,206

[45] Date of Patent: Oct. 6, 1987

[54] METHOD FOR DISINFECTING DENTAL IMPRESSIONS

[75] Inventor: Donald M. Nevin, Woodbury, N.Y.

[73] Assignee: Buffalo Dental Manufacturing Co., Inc., Syosset, N.Y.

[21] Appl. No.: 774,772

[22] Filed: Sep. 11, 1985

[51] Int. Cl.$^4$ .............................................. A61L 2/00
[52] U.S. Cl. ................................... 422/24; 422/186.3
[58] Field of Search ...................... 422/24, 28, 32, 33, 422/186.3; 210/192

[56] References Cited

U.S. PATENT DOCUMENTS

| | | | |
|---|---|---|---|
| 1,965,947 | 7/1934 | Prouty . | |
| 2,056,614 | 10/1936 | Moehler | 422/186.3 |
| 2,058,826 | 10/1936 | Reece | 99/247 |
| 2,245,762 | 6/1941 | De Stefani et al. | 250/45 |
| 2,253,250 | 8/1941 | Selig | 250/52 |
| 2,407,379 | 9/1946 | Morehouse | 422/24 X |
| 2,592,131 | 4/1952 | Farrar | 250/51 |
| 2,822,476 | 2/1958 | Osgood | 250/51 |
| 3,776,694 | 12/1973 | Leittl | 422/186.3 |
| 3,852,032 | 12/1974 | Urbach | 422/24 |
| 3,955,922 | 5/1976 | Moulthrop | 422/186.3 |
| 4,448,750 | 5/1984 | Fuesting | 422/24 X |

FOREIGN PATENT DOCUMENTS 2320990 10/1974 Fed. Rep. of Germany ........ 422/24

OTHER PUBLICATIONS

"Guidelines for Infection Control in the Dental Office and the Commercial Dental Laboratory", JADA, 110, 969 (1985).

Primary Examiner—Tom Wyse
Attorney, Agent, or Firm—Nolte, Nolte and Hunter

[57] ABSTRACT

A method for disinfecting a dental impression. The impression is exposed to a germicidally effective amount of ultraviolet light within a drawer in a box-like apparatus. The interior of the housing is mirrored, and supports are provided for holding the dental impression above a flat horizontal mirrored surface within the drawer as the drawer is moved inwardly and outwardly of the housing. The ultraviolet light is provided within the drawer when the drawer is closed, so that at least a portion of the ultraviolet light is reflected off of the horizontal mirrored surface and against the bottom of the dental impression.

11 Claims, 7 Drawing Figures

METHOD FOR DISINFECTING DENTAL IMPRESSIONS

BACKGROUND OF THE INVENTION

This invention relates to a method of disinfecting dental impressions and to a preferred apparatus for carrying out the method.

In order to prevent the transmission of diseases from dental patients to their dentists and the dentists' assistants and technicans, time consuming and costly procedures have been followed to disinfect all the tools and materials with which the patients come in contact, particularly the tools and materials having the patients' blood and saliva on them which can carry high concentrations of potentially infective viruses and bacteria. The principal means for disinfecting dental tools and materials have been steam autoclaves, ovens, ethylene oxide gas, boiling water and chemical disinfectants, such as chlorine solutions, formaldehyde, glutaraldehyde and iodophors.

However, problems have been encountered in disinfecting dental impressions. Generally, dental impressions have first been rinsed with water to remove the patients' blood and saliva, and then, they have been disinfected with chemical agents which will not react with the plastic impression materials utilized or the plastic or metal trays which hold the impression materials. However, chemical disinfectants have tended to distort, crack and/or weaken the surfaces of impression materials when the impression materials have been exposed for too long a time to the disinfectants. As a result, the selection of the disinfectant chemicals and the length of time that the impression materials are exposed to the disinfectant chemicals have had to be closely controlled to avoid damaging the impression materials.

There has been a need, therefore, for a way of routinely disinfecting dental impressions in a simple and low cost manner that does not risk damaging the impression materials.

SUMMARY OF THE INVENTION

In accordance with this invention, a method is provided for disinfecting a surface of a dental impression comprising: exposing the surface of the impression to a germicidally effective amount of ultraviolet light.

DETAILED DESCRIPTION OF THE PREFERRED EMBODIMENTS

Figure 1:
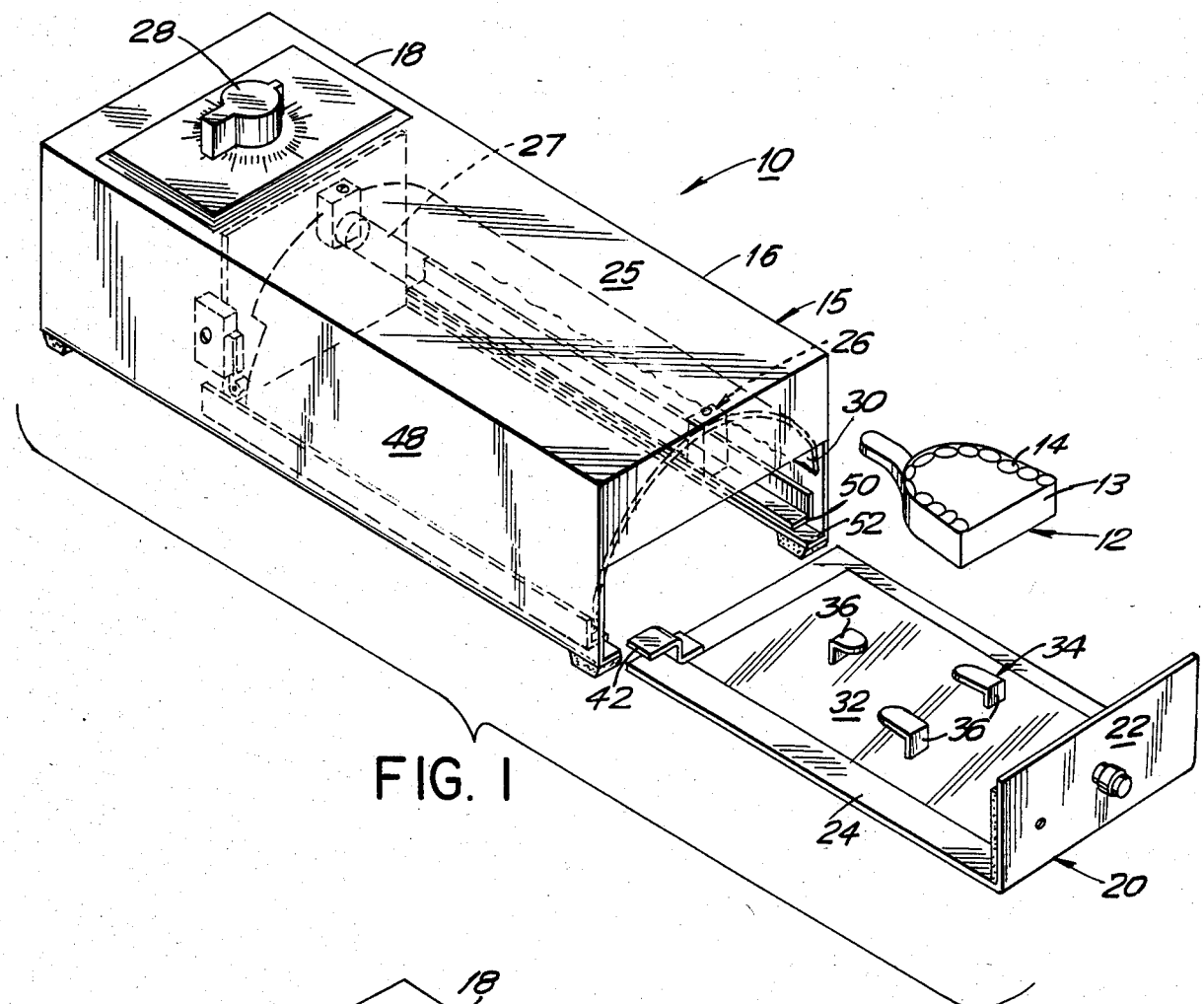
FIG. 1 is an exploded perspective view of an apparatus for exposing a dental impression to ultraviolet-light in order to disinfect the impression.
Figure 2:
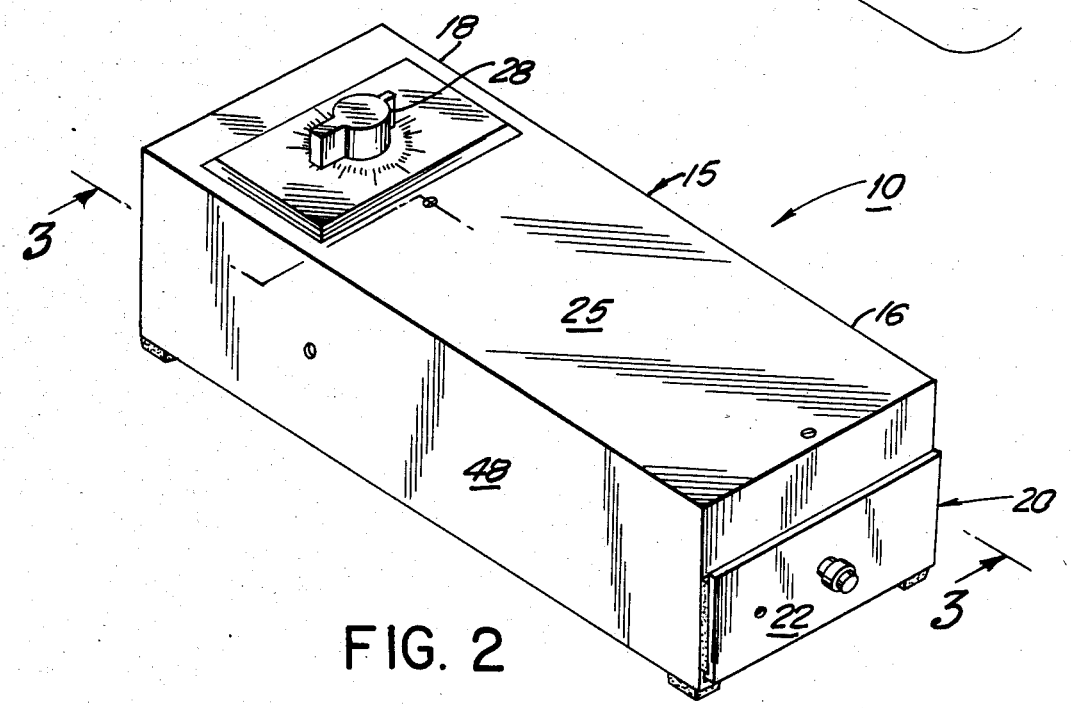
FIG. 2 is a perspective view of the apparatus of FIG. 1.

Shown in FIGS. 1-5 is a preferred apparatus, generally 10, for disinfecting a dental impression, generally 12, by the method of this invention. The dental impression 12 comprises a conventional impression tray 13 made from metal (e.g., aluminum) or plastic (e.g., acrylic or polyethylene) which contains a conventional cured plastic impression material 14. The dental impression 12 can be placed within the apparatus 10 and then exposed to ultraviolet light which will destroy potentially infective viruses and bacteria on the surfaces of the impression 12 and its tray 13 and impression material 14.

As best seen from FIG. 1, the apparatus 10 includes a box-like housing 15 that is divided into a front compartment 16 and a rear compartment 18. A drawer 20 is provided in the front compartment 16 of the housing 15. The drawer 20 can be pulled outwardly of the front of the housing 15 to open the drawer, so that the dental impression 12 can be placed within the drawer 20. The drawer 20 can also be pushed inwardly of the front of the housing 15 to close the drawer so that the dental impression 12, within the drawer, is inside the front compartment 16. As shown in FIG. 1, the drawer 20 can comprise a simple upstanding front member 22 and a horizontal bottom member 24 which is attached to the bottom of the front member 22 and extends rearwardly therefrom. The bottom member 24 forms the bottom wall of the front compartment 16 when the drawer 20 is closed. Preferably, the drawer 20 is not provided with upstanding side and rear members on the bottom member 24.

Figure 3:
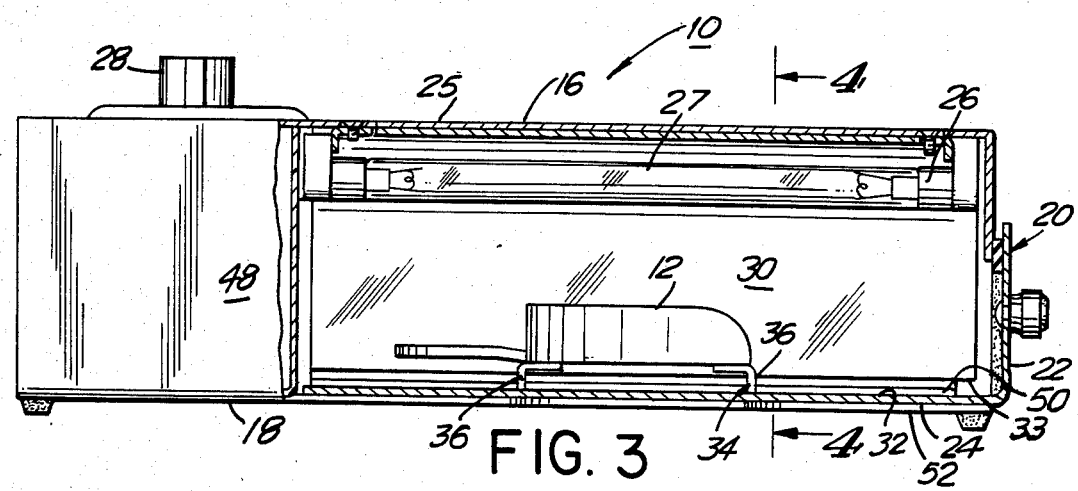
FIG. 3 is a side view of the apparatus of FIG. 2, taken partly in section along line 3—3 in FIG. 2.
Figure 4:
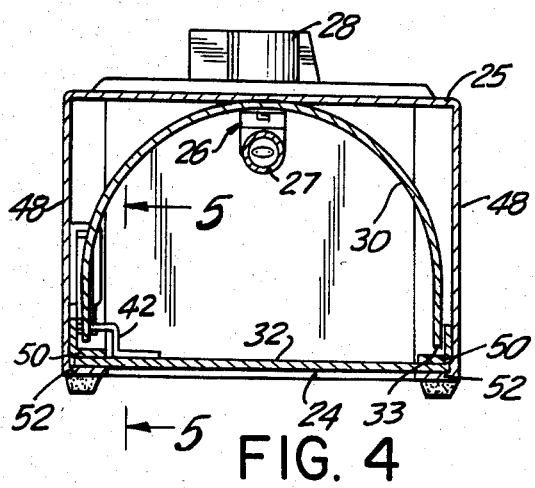
FIG. 4 is a sectional view, taken along line 4—4 in FIG. 3.

As best shown in FIGS. 3 and 4, the front compartment 16 of the apparatus 10 contains, adjacent its top wall 25, at least one ultraviolet radiation lamp, generally 26. Preferably, the ultraviolet lamp 26 has an elongated clear glass tube 27 that has an ultraviolet light-emitting filament therein and that extends from front to rear in the front compartment 16. The lamp 26 is electrically connected in a conventional manner at its rear to a source of electric power (not shown) and to a timer 28 in the rear compartment 18. The timer 28 is adapted to connect the lamp 26 with the source of electric power for a pre-selected time period. When the timer 28 is activated, electric power is supplied to the lamp 26 so that its tube 27 emits ultraviolet light until the selected time period, preset on the timer 28, has elapsed. Then, the power to the lamp 26 through the timer 28 will be interrupted, and the tube 27 will be de-energized and will discontinue emitting ultraviolet radiation.

In accordance with this invention, the structure of the lamp 26 is not critical, and any conventional germicidal ultraviolet lamp can be utilized such as a lamp with an ultraviolet light power output of up to about 6000 microwatts per square centimeter. It is preferred that the lamp 26 in the apparatus 10 have an ultraviolet light power output of at least about 100 microwatts per square centimeter, preferably at least about 600 microwatts per square centimeter, up to about 2500 microwatts per square centimeter, such as is produced by a conventional 6 watt ultraviolet lamp having a peak energy output at about 254 nanometers. The structure of the timer 28 also is not critical, and any conventional timer can be used such as one which can provide a pre-selected time of up to about one-half hour of exposure of the dental impression 12 to ultraviolet light generated by the lamp 26 in the apparatus 10.

As best shown in FIGS. 1, 3 and 4, the interior of the front compartment 16 of the apparatus 10 is mirrored. Upper and lower surfaces 30 and 32, respectively, are provided in the front compartment 16 to reflect ultraviolet light generated by the lamp 26 within the front compartment. The upper surface 30 preferably is a concave downward, smooth mirrored surface which is located above the lamp 26 and its tube 27 and which extends downwardly, symmetrically about the axis of the tube 27 along the length of the tube. The lower surface 32 preferably is a flat smooth horizontal mirrored surface on top of the bottom member 24 of the drawer 20 which also extends along the length of the tube 27 of the lamp 26, below the tube. Preferably, the lower surface 32 lies just beneath the bottom edges 33 of the upper mirrored surface 30.

On top of the lower mirrored surface 32 on the bottom member 24 of the drawer 20 are provided means, generally 34, for supporting the dental impression 12 above the lower mirrored surface 32 when the drawer 20 is within the front compartment 16 and when the drawer 20 is being moved inwardly or outwardly of the front compartment 16. As best shown in FIGS. 1 and 3, such support means 34 preferably comprise a plurality of spaced apart stand-offs 36 on top of the lower mirrored surface 32, upon which the bottom of the dental impression 12 can be placed. The stand-offs 36 hold the dental impression 12 above the lower mirrored surface 32, even when the drawer 20 is moved inwardly or outwardly of the front compartment 16. As a result, the bottom surface of the dental impression 12 can be exposed to ultraviolet light from the lamp 26, reflected off of the lower mirrored surface 32, when the lamp 26 is turned on to disinfect the impression within the closed drawer 20 of the apparatus 10.

Figure 6:
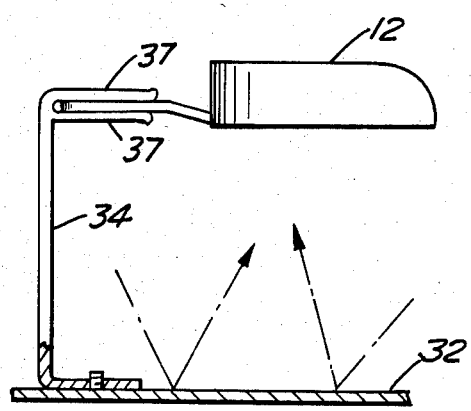
FIG. 6 is a fragmentary side view, showing an alternative embodiment of a device for holding a dental impression within the apparatus of FIGS. 1-5.

As shown in FIG. 6, the support means 34 can alternatively comprise a pair of substantially parallel, horizontal fingers 37. The fingers 37 are supported above the lower mirrored surface 32 and are biased towards one another. As a result, the fingers 37 can grasp between them the dental impression 12 and hold it in place above the lower mirrored surface 32.

Figure 7:
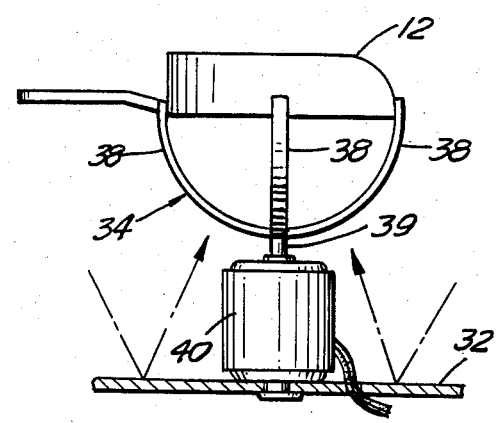
FIG. 7 is a fragmentary side view, showing another alternative embodiment of a device for holding a dental impression within the apparatus of FIGS. 1-5.

As shown in FIG. 7, the support means 34 can alternatively comprise a plurality of upstanding fingers 38. The bottoms of the fingers 38 are connected to a common vertical shaft 39 that is connected to a conventional electric motor 40. The motor 40, in turn, is connected to a source of electric power (not shown). The tops of the fingers 38 are adapted to grasp the dental impression 12 and hold it above the lower mirrored surface 32. The fingers 38 also horizontally rotate the dental impression 12 when power is supplied to the electric motor 40 to rotate the shaft 39. By rotating the dental impression 12, the upstanding fingers 38 permit the dental impression to be more evenly exposed to ultraviolet light generated by the lamp 26 within the apparatus 10.

Figure 5:
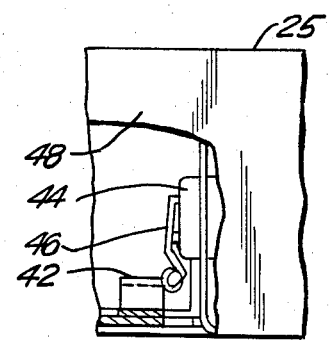
FIG. 5 is a partial sectional view, taken along line 5—5 in FIG. 4.

As best shown in FIGS. 1, 4 and 5, an upstanding finger 42 is provided at the rear of the bottom member 24 of the drawer 20, and a switch 44 is provided at the rear of the front compartment 16 above the finger 42. The switch 44 controls the connection between the source of electric power (not shown) and the lamp 26, as well as the optional motor 40. The switch 44 has a depending finger 46 which is located behind the upstanding finger 42 and is urged frontally of the switch 44. When the drawer 20 is moved rearwardly to close it, the upstanding finger 42 on the drawer 20 is moved rearwardly with the drawer 20 causing the upstanding finger 42 to move the depending finger 46 rearwardly, thereby activating the switch 44 so that electric power can be supplied to the ultraviolet lamp 26, as well as the motor 40, when the timer 28 is actuated. The switch 44 disconnects the lamp 26 and motor 40 from their electric power source when the drawer 20 is not closed and its upstanding finger 42 is not urging rearwardly the depending finger 46 on the switch 44.

As best shown in FIGS. 1 and 4, the bottom of each of the side walls 48 of the front compartment 16 is provided with a pair of parallel horizontal upper and lower guides 50 and 52, respectively, between which the sides of the bottom member 24 of the drawer 20 can slide frontally and rearwardly. Movement of the drawer 20 in and out of the front compartment 16 results in substantially horizontal movement of its bottom member 24 between the upper and lower guides 50, 52 and corresponding substantially horizontal movement of the supporting means 34 and the dental impression 12 thereon in and out of the front compartment 16 of the apparatus 10.

The apparatus 10 can be used to disinfect the surfaces of any conventional dental impression 12 so that the impression can then be (1) safely handled and (2) used to manufacture high quality dentures to close tolerances. In this regard, it is believed that the surfaces of conventional impression materials 14, such as the silicone rubber, rubber, alginate and zinc oxide impression materials, are not significantly distorted, cracked or weakened by exposure in the apparatus 10 to as much as about 6000 microwatts of ultraviolet light power per square centimeter for up to about 10 minutes, preferably no more than about 2500 microwatts of ultraviolet light power per square centimeter for up to about two minutes. It is preferred that the surfaces of dental impression materials be exposed in accordance with this invention to at least about 12,000 microwatt seconds per square centimeter, preferably at least about 36,000 microwatt seconds per square centimeter, of ultraviolet light energy, in order to disinfect them so that they can then be safely handled without adversely affecting their surfaces or the quality of dentures made from them.

It is thought that this invention and many of its attendant advantages will be understood from the foregoing description and that it will be apparent that various changes can be made in the steps of the method for disinfecting a dental impression and in the apparatus 10 for carrying out the method without departing from the spirit and scope of the invention or sacrificing all of its material advantages, the method and apparatus hereinbefore described being merely preferred embodiments. In this regard, terms such as "front", "rear", "upper", "lower", "horizontal", "above" and "below" are used herein as relative terms to describe the apparatus 10 in FIGS. 1–7 and in the claims which follow.

I claim:

1. A method for disinfecting a surface of a dental impression comprising exposing the surface of the impression to but no more than about 2500 microwatts of ultraviolet light power per square centimeter for up to about 2 minutes.

2. The method of claim 1, wherein the surface of the dental impression is exposed to at least about 12,000 microwatt seconds of ultraviolet light energy per square centimeter.

3. The method of claim 2, wherein the surface of the dental impression is exposed to at least about 36,000 microwatt seconds of ultraviolet light energy per square centimeter.

4. The method of claim 1, wherein the dental impression is exposed to the ultraviolet light within a housing of an apparatus comprising:

a drawer which can be moved outwardly and inwardly of the housing to open and close the drawer and within which the dental impression can be placed for insertion within, and removal from, the interior of the housing; the drawer having within it a first mirrored surface and means for supporting the dental impression above the first mirrored surface within the drawer as the drawer is moved inwardly and outwardly of the housing; and means for providing the ultraviolet light within the drawer above the first mirrored surface when the drawer is closed, so that at least a portion of the ultraviolet light is reflected off of the first mirrored surface and against the bottom of the dental impression.

5. The method of claim 4, wherein a second smooth mirrored surface is provided within the housing above the light providing means when the drawer is closed.

6. The method of claim 5, wherein the second mirrored surface comprises a concave downward surface which extends downwardly symmetrically about the light providing means.

7. The method of claim 6, wherein the light providing means comprises a lamp with a horizontally elongated, ultraviolet light-emitting tube in the housing and the second mirrored surface extends downwardly symmetrically about the axis of the tube along the length of the tube.

8. The method of claim 7, wherein the first mirrored surface is a flat smooth horizontal surface just beneath the bottom of the second mirrored surface.

9. The method of claim 4, wherein the supporting means comprises a plurality of spaced apart stand-offs on top of the first mirrored surface for holding the bottom of the dental impression above the first mirrored surface as the drawer is moved inwardly and outwardly of the housing.

10. The method of claim 4, wherein the supporting means comprises a pair of substantially parallel horizontal fingers which are supported above the first mirrored surface and are biased towards one another so that they can grasp between them the dental impression and hold it in place above the first mirrored surface.

11. The method of claim 4, wherein the supporting means comprises: a plurality of upstanding fingers, the bottoms of which are connected to a common vertical shaft and the tops of which are adapted to grasp the dental impression and to rotate it when the shaft is rotated; and means for rotating the shaft when the light providing means is providing ultraviolet light within the drawer.

* * * * *